(12) United States Patent
Kenet

(10) Patent No.: US 7,522,825 B2
(45) Date of Patent: Apr. 21, 2009

(54) METHOD AND DEVICE FOR SKIN CANCER SCREENING

(76) Inventor: Robert Kenet, 710 Park Ave., Apt. 9D, New York, NY (US) 10021

( * ) Notice: Subject to any disclaimer, the term of this patent is extended or adjusted under 35 U.S.C. 154(b) by 489 days.

(21) Appl. No.: 10/894,906

(22) Filed: Jul. 20, 2004

(65) Prior Publication Data
US 2004/0258288 A1 Dec. 23, 2004

Related U.S. Application Data

(62) Division of application No. 09/782,851, filed on Feb. 14, 2001, now Pat. No. 6,792,137.

(60) Provisional application No. 60/183,551, filed on Feb. 18, 2000.

(51) Int. Cl.
*G03B 29/00* (2006.01)
*G01J 4/00* (2006.01)

(52) U.S. Cl. .............................. 396/14; 356/364; 606/9

(58) Field of Classification Search .................. 396/14, 396/15; 356/364, 369; 600/407, 476; 606/9; 348/77
See application file for complete search history.

(56) References Cited

U.S. PATENT DOCUMENTS

| | | | |
|---|---|---|---|
| 3,567,309 A * | 3/1971 | Jasgur | 359/386 |
| 5,016,173 A | 5/1991 | Kenet et al. | |
| 5,291,889 A | 3/1994 | Kenet et al. | |
| 5,294,948 A * | 3/1994 | Merkt et al. | 396/544 |
| 5,836,872 A | 11/1998 | Kenet et al. | |
| 5,836,877 A | 11/1998 | Zavisian | |
| 6,018,590 A | 1/2000 | Gaborski | |
| 6,032,071 A * | 2/2000 | Binder | 600/476 |
| 6,106,457 A * | 8/2000 | Perkins et al. | 600/175 |
| 6,215,893 B1 | 4/2001 | Leshem et al. | |

* cited by examiner

*Primary Examiner*—Christopher Mahoney
(74) *Attorney, Agent, or Firm*—Davidson, Davidson & Kappel, LLC

(57) ABSTRACT

A method for providing a preliminary diagnosis of skin cancer, more specifically a screening risk assessment of pigmented lesions receiving digital photographs of skin abnormalities from a plurality of consumers at a server, receiving medical information related to each of the plurality of consumers at the server, assigning an identification to at least one of the consumers and the digital photographs, reviewing the digital photographs and categorizing the digital photographs into at least three categories so as to define category information, the at least three categories including a first category of a first risk, a second category of risk lower than the first category and a third category of insufficient photograph quality, and providing the category information as a function of the identification. The digital photographs may be of pigmented skin lesions and may be clinical photographs or may utilize the optical technique of epiluminescence microscopy (ELM) to visualize pigmented or capillary structure below the skin surface that are not visible to the naked eye.

10 Claims, 4 Drawing Sheets

METHOD AND DEVICE FOR SKIN CANCER SCREENING

RELATED APPLICATION

The present application is a divisional of U.S. application Ser. No. 09/782,851, filed Feb. 14. 2001, which claimed priority from U.S. Provisional Application 60/183,551, filed Feb. 18, 2000, the entire disclosure of which is hereby incorporated by reference. The present application claims priority from U.S. Provisional Application No. 60/183,551 filed Feb. 18, 2000, the entire contents of which are hereby incorporated by reference herein.

BACKGROUND OF THE INVENTION

1. Field of the Invention

The present invention relates generally to dermatology and more particularly to a method and device for aiding in screening populations of patients for skin cancer.

2. Background Information

Skin cancer, the most deadly form of which is melanoma, typically is diagnosed by a dermatologist examining pigmented skin lesions (colloquially known as "moles") and/or other skin abnormalities on a patient. Typically, a dermatologist makes a determination based on visual inspection of each skin lesion's morphology, whether it is likely to be skin cancer or a potential precursor of skin cancer. This determination is made in the context of a patient's clinical history, risk factors for skin cancer, and other information. The dermatologist then decides if a pigmented lesion should the excised for histopathological evaluation.

Cutaneous melanoma starts growing in the top layer of the skin—the epidermis. If it is detected and completely removed while still confined to the epidermis, it can be completely cured, and has a very high cure rate if it has just entered the next skin layer, the papillary dermis. Thus screening and early detection are critical to lowering the morbidity and mortality of this cancer that has been increasing rapidly in incidence and is one of the most common cancers of young people, especially young women.

In 1992 a Consensus Conference sponsored by the National Institutes of Health recommended that skin cancer screening be initiated in the United States, but recognized that primary care physicians do not have sufficient training to perform it well.

If screening is attempted by those without sufficient experience, early melanomas may be missed and too many unnecessary biopsies may be performed.

SUMMARY OF THE INVENTION

It is an object of the present invention to improve access of potential patients to skin cancer screening experts using the Internet, thus enabling more efficient and cost-effective screening of large patient populations. It is a further object of this invention to empower consumers to assist in screening and monitoring their own skin and that of their family members, with guidance from skin cancer experts.

It is a further object of this invention to provide for consumers a digital epiluminescence microscopy (ELM) camera or a digital ELM lens attachment or lens stand that they may used with a digital or analog camera at home to obtain ELM photographs of pigmented lesions on their skin. ELM can improve the accuracy of screening and can help identify early, curable melanoma and benign lesions that mimic melanoma.

In the present invention, consumers may submit digital photographs of their pigmented lesions for clinical inspection by experts using digital cameras that they have at home. Alternatively, for a more accurate skin cancer risk assessment, they may submit photographs obtained with a special optical technique called epiluminescence microscopy (ELM). In this invention, two methods of performing ELM at home will be available to the consumer. In the first technique, the consumer will be instructed to wet their skin using water, alcohol, or oil. This will permit a crude type of ELM image by decreasing refractive-index mismatch at the air-skin interface, allowing visualization of some pigmented structures below the skin surface. The second technique requires a special ELM lens attachment that is also a subject of the present invention.

The present applicant has several patents issued or applications pending related to digital. ELM and/or other aspects of monitoring the skin for skin cancer, particularly melanoma. For example U.S. Pat. No. 5,836,872 discloses a method and apparatus for in vivo monitoring of skin surfaces of the body to aid in the diagnosis of skin cancers. A digital ELM image, obtained under standardized conditions, enables in vivo visualization of pigmented or capillary features within the skin otherwise not visible to the eye. The device and method of the above-mentioned patent can aid a dermatologist or other skilled professional in diagnosing melanoma or other skin cancers. These features may be clues to early melanoma or to the presence of a melanoma mimicker that does not need surgery.

Early melanomas can be difficult to recognize since they may look similar to certain benign lesions. Moreover, many benign lesions may look like melanomas. Thus, screening is best performed by dermatologists or other physicians with expertise in skin cancer screening. If ELM-based screening is available the accuracy and cost-effectiveness may be improved further.

Dermatologists however, only see a small fraction of the potential number of patients that need to be screened. For example, in the United States there are only about 8000 dermatologists, but hundreds of thousands of primary care physicians. Thus many patients, in the U.S. and other countries, who need to be screened do not have access to a dermatologist and rely on primary care providers.

The Internet has recently become a leading source of medical information for consumers and holds promise for improving access of patients to both primary care providers and to specialists. Digital cameras are becoming widely available which provide the possibility for consumers to take digital photographs of their own skin lesions and transmit them to experts. Likewise, traditional analog photographs can be scanned so as to form digital images and sent to experts.

The present invention provides a method for providing a preliminary diagnosis of skin cancer, more specifically a screening risk assessment for individual pigmented skin lesion, comprising the steps of:

receiving digital photographs of skin abnormalities from a plurality of patients at a server;

receiving medical information related to the plurality of patients at the server;

assigning an identification to each of the plurality of patients;

reviewing the digital photographs and categorizing the skin abnormalities in the digital photographs into at least three categories so as to define category information, the at least three categories including a first category of a first risk, a second category of risk lower than the first category and a third category of insufficient photograph quality; and providing the category information as a function of the identification.

The method of the present invention can permit a skilled physician to review the clinical and/or ELM digital photographs from a patient anywhere in the world, and quickly make a screening diagnosis or risk assessment for each photographed pigmented skin lesion.

Advantageously, the server may contain. HTML-based pages of information, herein defined as the web pages. The web pages preferably are accessible to the public via the Internet, and contain information on the type of cameras preferable for digital photography with the method of the present invention, including, for example, information on proper photographic techniques for macrophotography of the skin, and ELM techniques such as placing oil, or other liquid, on the skin or using a special lens adapter with crossed polarizing filters. Users, preferably will submit clinical information related to their skin cancer history or risk factors by entering the information into predefined fields on the web pages.

However, the server may also contain HTML- or other computer language-based pages that reside on a server accessible through a private communications network, such as a LAN or WAN. This embodiment can increase the security of the present method.

Preferably, credit card or account information is received along with each photo. Standard e-commerce software may be included at the server to approve credit card submissions.

Information transmitted from and to the clients preferably is transmitted using a secure encryption technology, such as RSA encoding or other types of public key encryption methods. All web pages related to patient information preferably will use the best available security methods, such secure socket layer (SSL) technology or other as may be, or may become, the standard for medical information security as required for compliance with Health Care Financing Administration (HCFA) or other government regulations.

In a preferred embodiment of the present invention consumers may submit clinical information by filling out a questionnaire and they may submit digital photographs and/or digital ELM photographs of their skin and pigmented lesions on their skin.

Two elements of a patient's or consumer's risk of melanoma may be estimated via information they submit to health care providers via the Internet—(1) a patient's overall risk of developing melanoma, (2) each pigmented lesion's risk of being melanoma (or becoming) melanoma.

One important question that can divide patients into two groups of higher or lower risk of developing melanoma is—"Do you tan with ease? Yes or No". Patients that answer "No" have been called "melano-incompetent" and those that answer "Yes" have been called "melano-competent" by the dermatologist, Thomas B. Fitzpatrick MD. This is a simplification of his four category skin type. Other questions regarding family history, sun exposure, number of moles, etc. can be used to develop an overall assessment of a patient's risk of developing melanoma.

Thus, the medical information submitted by the consumer preferably includes a listing of skin cancer history and risk factors, such as (1) "melano-competance," defined as those that tan with ease or "melano-incompetence," defined as those that do not tan with ease (2) other descriptions of skin type (such as Fitzpatrick types 1 through 4) (3) patient age, (4) family history of melanoma or non-melanoma skin cancer, (5) personal medical history, (6) body location of each submitted pigmented lesion, (7) an estimate of the total number of pigmented lesions on each patient, and (8) clinical information on each submitted pigmented lesion, such as any clinical change.

Then digital photographs submitted with or without ELM will be used to provide a screening risk assessment of individual pigmented lesions.

The present applicant has developed strategies for using ELM to help stratify the risk of individual pigmented lesions into one of several categories, in lieu of its typical use to make a preliminary diagnosis. For example, one possible set of categories with progressive probabilities that a pigmented lesion may be melanoma based on their ELM features is as follows:

1. Risk Level 1—clearly benign, such as a seborrheic keratosis, hemangioma, dermal nevus, blue nevus, Spitz nevus or other potential melanoma mimicker;
2. Risk Level 2—low risk melanocytic, such as a flat, symmetric junctional nevus with a pigment network that is not too dark and that fades at the periphery;
3. Risk Level 3—Medium Risk melanocytic, such as an atypical (dysplastic/Clark's) nevus with a "patchy and/or pink" pigment network (these are potential melanoma precursors or markers),
4. Risk Level 4—Higher Risk melanocytic, such as a lesion with a pigment network where the darkest part of the network (even if not very dark) is at the lesion periphery, or where there are small irregular confluences of pigment overlying a generally irregular pigment network, or other ELM pattern suggesting that the lesion could be an early melanoma without all of the fully developed classical ELM features of melanoma (N.B. this group includes many atypical nevi in addition to some early melanomas and therefore has been referred to as "the gray-zone" by the applicant);
5. Risk Level 5—High Risk of being melanoma, e.g. lesions with fully developed or classically described ELM features of melanoma.

Other terms and groupings may be used for defining a risk stratification of pigmented lesions based on their clinical or clinical plus ELM features. For example, in one embodiment of the present invention consumers are screened for melanoma via digital photographs or digital ELM photographs that they submit to physician specialists via the internet. In this context one may choose to use a simpler set of categories with just two or three levels of "risk" plus a category that indicates insufficient technical quality of the images for a screening risk assessment or screening diagnosis.

If high quality digital ELM photographs are submitted by the consumer from home using an ELM lens attachment on their digital camera, then a more detailed categorization or risk-stratification, such as that above, may be used. On the other hand, if consumers only submit non-ELM digital snapshots of their skin then a very simple categorization or risk-stratification for each pigmented lesion may be used.

Snapshots of regions of a consumer's skin ("regional photograph") may be submitted, and the count of number of pigmented lesions can also be used as one important factor is determining a patient's general risk for melanoma, since it is known that patients with many pigmented lesions are at higher risk of melanoma. These snapshots may also be used to direct the consumer to take a close-up photograph for ELM photograph of particular lesions seen in the regional photograph.

The e-mail address of each user or another identifier (a random number, or perhaps even name, address, social security number, local physician name and phone number, etc. for those patients/consumers who do not mind this degree of identification) are also preferably provided. The web pages also preferably include a submission button that the client clicks to submit a photograph. The user can then choose an image file to forward or acquire an image from a digital camera or from a video camera or other imaging device attached to the user's computer. The image preferably is stored as a jpeg, .gif or .tiff file. However, the server preferably is equipped to handle almost all image files available to the public. The quality of the image submitted should be high, but the exact quality need not be a specific resolution, as the reviewing physician can decide whether the quality is insufficient.

Preferably the reviewing physician has a computer that can view a display page with the patient information. The display page may be located on the server as well and be accessible through a password via the Internet, or may be accessible via a private connection, for example a virtual private network.

The server may be for example a WINDOWS NT-based server containing a relational database and a central processing unit, for example a PENTIUM III available commercially processor from the Intel Corporation.

The display page can provide the reviewing physician with at least three options, a first risk, a lower risk and insufficient quality. Optionally, a forth or other category may be included, such as a category indicating "medium risk" or a category indicating that the lesion is in an indeterminate risk group or in a "gray-zone." If the quality is insufficient, the diagnostician clicks that choice, which is for example a button on a web page. The client then is sent an e-mail, either automatically or by an employee of the service provider stating that the quality is insufficient. The client can then be directed to a service assistance pages which identifies common problems with digital photography of pigmented skin lesions. The server assistance pages may include an information page providing a list of types of cameras and problems or hints associated with each camera.

The present invention also provides a system for providing a preliminary diagnosis of skin cancer comprising a server storing a plurality of information pages. The server includes at least one first information page for permitting submission of a plurality of digital photographs of skin abnormalities to a server, medical information related to each of the plurality of digital photographs, and a client identification for each patient or each of the plurality of digital photographs associated with each patient and with each submitted pigmented lesion on each patient. The server also includes at least one second information page including a first of the plurality of digital photographs, the medical information related to the first digital photograph and a categorization section including a first category of a first risk, a second category of risk lower than the first category and a third category of insufficient quality. Optionally, one or more additional risk levels may be included, such as a "medium risk" level or and indeterminate risk level, or a "gray-zone." The client identification preferably is an e-mail address. The server also preferably includes an e-commerce program, such as that available from the Microsoft Corporation, for receiving credit card information from users who submit information.

The server also preferably includes a database, such as a relational database commercially available from Oracle or the Microsoft Corporation. While the server has been described as a single device, it could be comprised of two or more processors or devices.

It is a further object of this invention to make available to consumers at home a low cost lens attachment or lens stand that they may use to obtain ELM photographs of their pigmented lesions. This permits the consumers to submit more detailed visual information about the in vivo gross pathology of their pigmented lesions via the Internet to a skin cancer screening expert located at a remote location. Such information will allow the skilled skin cancer expert to provide a more accurate preliminary diagnosis or screening risk assessment.

Such lens attachment or lens stand may consist of a clear plastic cylinder with a magnifying lens at the top. The magnifying lens preferably will have a magnification of 4× to approximately 10× or other magnification chosen to match the lens of the digital camera used by the consumer. The clear plastic of the cylinder preferably will contain within it, just inside it, or surrounding it, a cylinder of plastic linear polarizing material with the polarization axis parallel to the circular cross-section of the cylinder.

A second polarizing filter will be within, above, or below the magnifying lens. The axis of this second polarizer should be orthogonal to the angle made by the location of the camera flash with respect to the cylindrical lens attachment or lens stand, such that the polarizing axis of the incident light to the skin will be orthogonal to the light reaching the digital camera sensor or analog camera film.

Thus this lens attachment will provide (1) magnification to facilitate macrophotography, (2) will provide a fixed distance between the skin and the camera lens, and (3) will provide crossed polarization photography as one form of ELM visualization of structures below the skin surface.

Alternatively, instead of using polarizing filters to perform ELM, the lens attachment or lens stand may provide a flexible membrane or transparent member that at its base that would smooth out any oil or liquid placed on the skin.

BRIEF DESCRIPTION OF THE DRAWINGS

An embodiment of the present system and method may be better understood with reference to the following figures in which.

DETAILED DESCRIPTION

Figure 1:
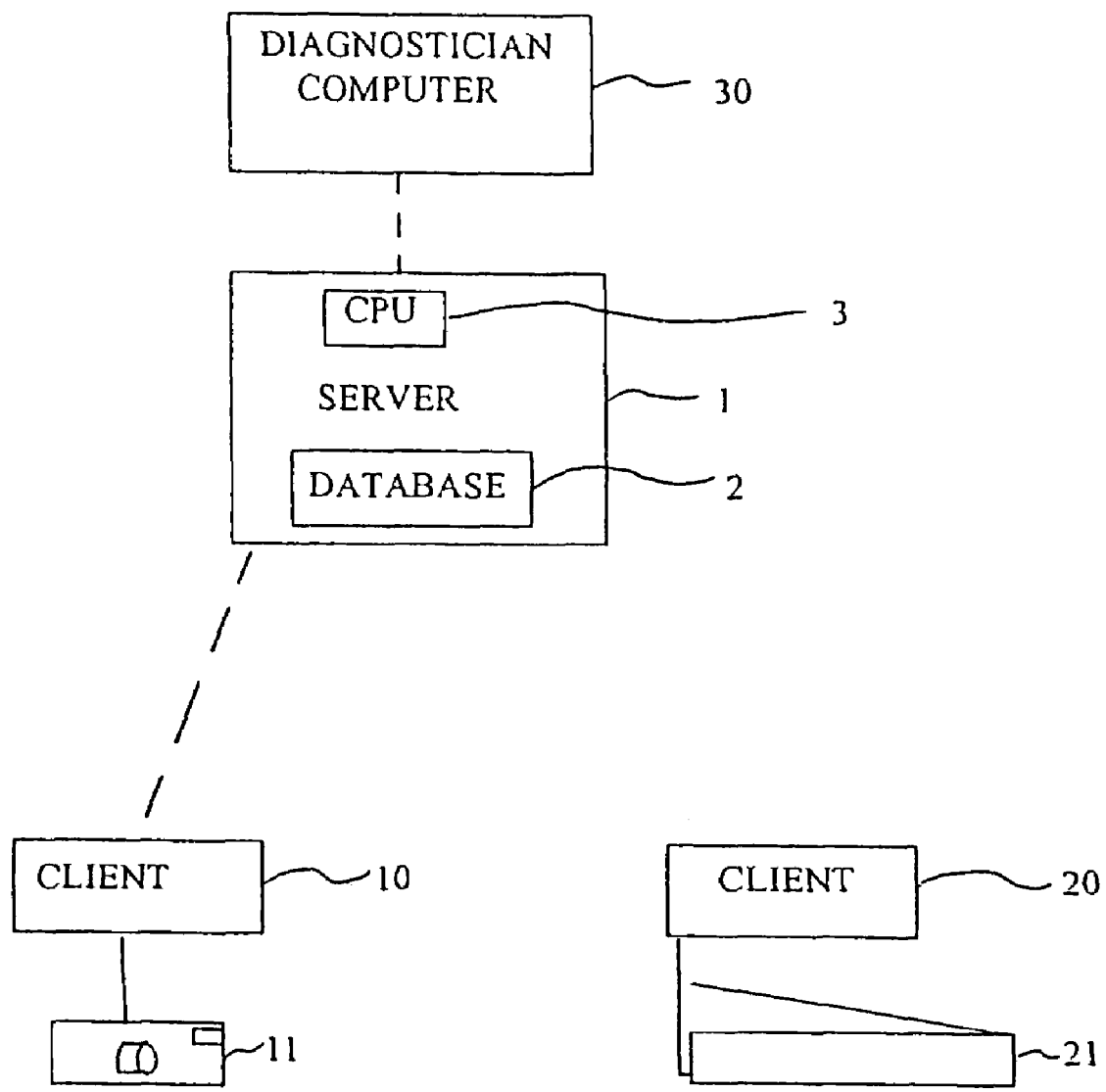
FIG. 1 shows a server used in the system of the present invention and clients which can use the method of the present invention.

FIG. 1 shows a server 1 having a database 2 and a central processing unit 3. The database 2 may be for example MICROSOFT ACCESS and the CPU a PENTIUM III processor.

Figure 2:
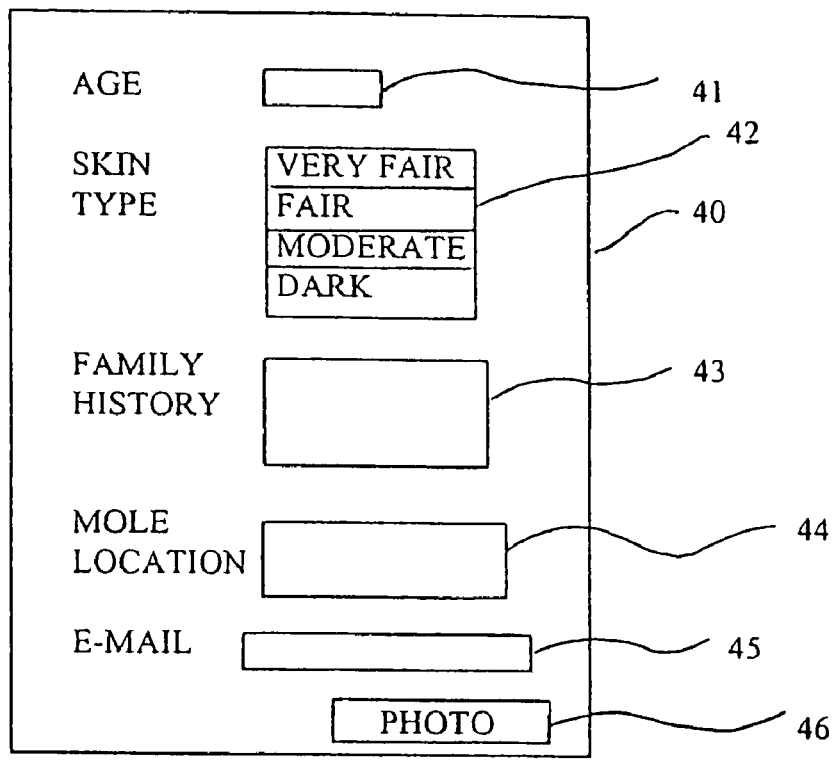
FIG. 2 shows an information page accessible by a client.

Server 1 is accessible, for example through the Internet and ISPs by clients 10, 20. Each client may view a page of information stored on the server 1, such as first submission page 40 shown in FIG. 2. As defined herein a page of information may be single or more than one page of information viewable on a screen. First submission page 40 includes data input fields 41, 42, 43, 44 and 45, for submitting age, skin type, family and personal history, pigmented lesion location and an e-mail address, respectively. Risk factor questions may be asked, as can questions about the lesion, such as whether the lesion has changed color or is growing. The data input fields may be blank spaces or may be a selection area with predefined choices, such as shown with skin type data input field 42. Other data input fields or different data may also be provided, such as eye color, susceptibility to sunburn, history of exposure to sun, etc.

Figure 5:
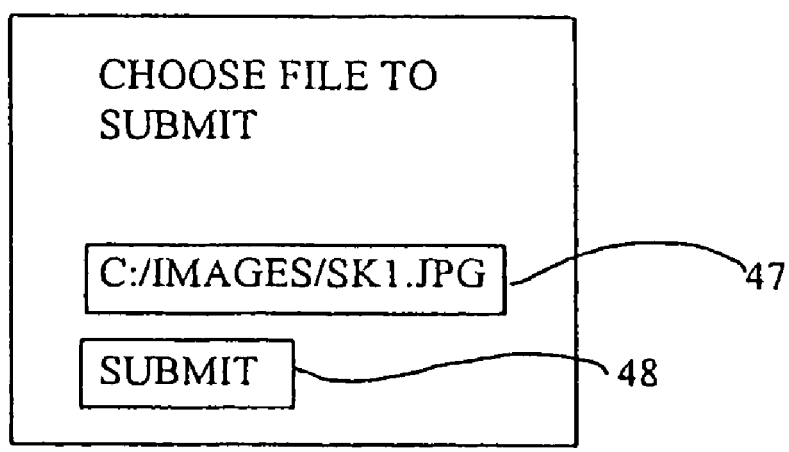
FIG. 5 shows an image acquisition or file selection page.

The first submission page 40 may also include a "submit photo" button 46, which prompts the user to enter a file with a digital image of a skin abnormality, as shown by page 47 of FIG. 5. Page 47 however may be directly included on page 40 as well. The digital images can be entered into client computer 10 for example by a digital camera 11, or for example into client computer or web viewer 20 by a scanner 21. The scanner may scan a regular photograph for example and convert it into a .jpeg file.

The user can then submit the information by clicking an information submission button 48. All information in the submission pages is thus submitted to the server 1 and stored in database 2, which has respective fields for the information and uses the e-mail address, and/or patient name with date of birth, for example, as the client identifier.

Preferably, the client is also prompted to enter in credit card or other payment information, for example health insurance information, along with the submitted information.

Figure 3:
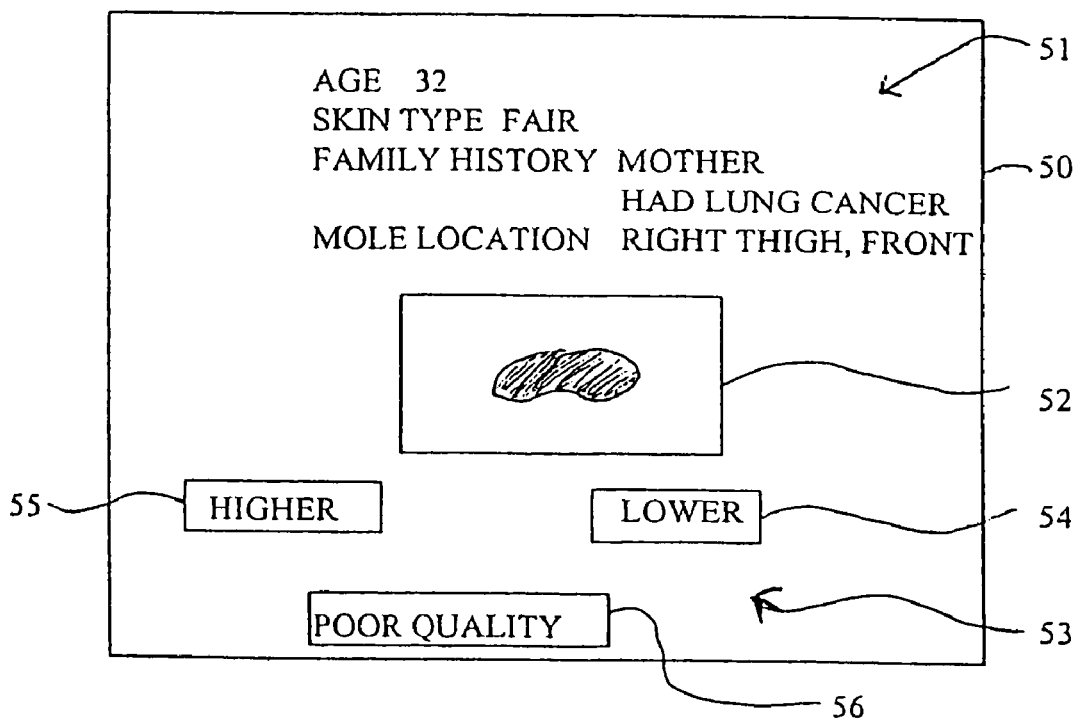
FIG. 3 shows an information page viewable by a physician.

A reviewing physician, trained in melanoma screening, can then access the data at computer or terminal 30, as shown in FIG. 1. Preferably, the physician must enter a password to review the data. The physician thus may view a display page 50 as shown in FIG. 3. Display page 50 has a medical information area 51 for displaying the medical information submitted by a client in fields 41, 42, 43, 44 of FIG. 2. Preferably, the client identifier entered in field 46 is not shown to the diagnostician to aid privacy. The digital photograph 52 of the skin abnormality is also displayed, as is a categorization section 53. Categorization section 53 preferably includes buttons including at least first risk button 54, higher risk button 55 and insufficient quality button 56. Preferably, the diagnostician also provides a variety of information including the overall image quality, the suspiciousness for melanoma, the suspiciousness for other skin cancer, the likelihood of being benign, the. likelihood of being an atypical nevus, and whether determination is impossible as being too difficult, even though the image quality is sufficient. The diagnostician can click one of the buttons, at which time an e-mail may be sent to the client informing them of the preliminary screening diagnosis or screening risk assessment. If high risk is selected, the e-mail preferably contains a list of information about how to proceed. Preferably, a zip code or other address information has been provided by the client and a list of dermatologists in the area is provided along with the e-mail.

Figure 4:
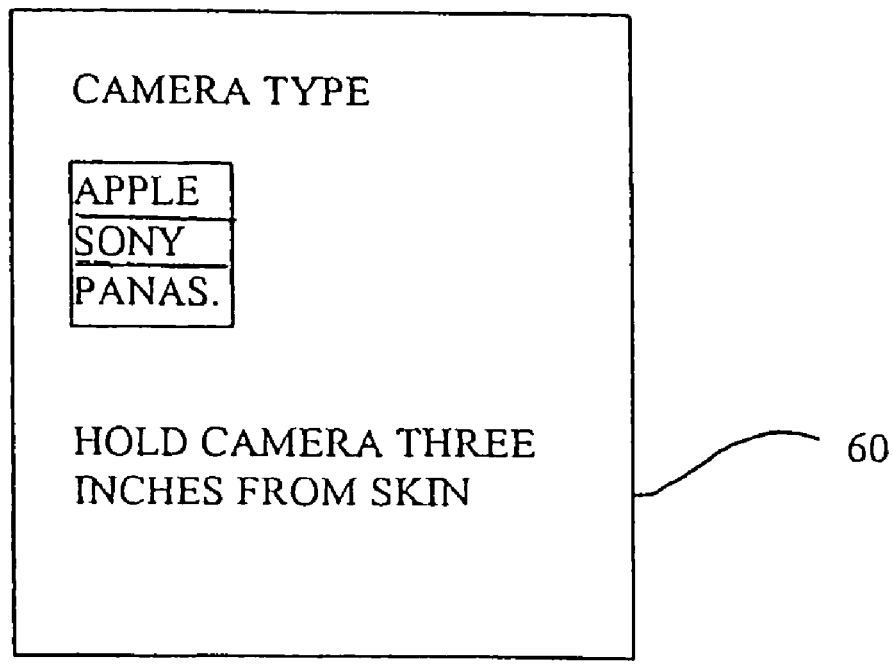
FIG. 4 shows a service assistance page.

If insufficient quality is selected, the user may be directed via e-mail to service pages 60, as shown in FIG. 4. The type of camera may be selected and tips may be provided on improving quality. Additionally or alternatively, photo 52 may also first be reviewed by a service person and the e-mail to the client may contain tips directly. In the case of submitted photographs that are of sufficient quality to perform a screening risk assessment, the credit card of the client preferably is charged a fee. The server may also include general information primary and secondary prevention of skin cancer and other information related to dermatology and skin care. Categories as defined herein may include the reviewing physician providing a written analysis and need not be provided by click buttons.

Figure 6:
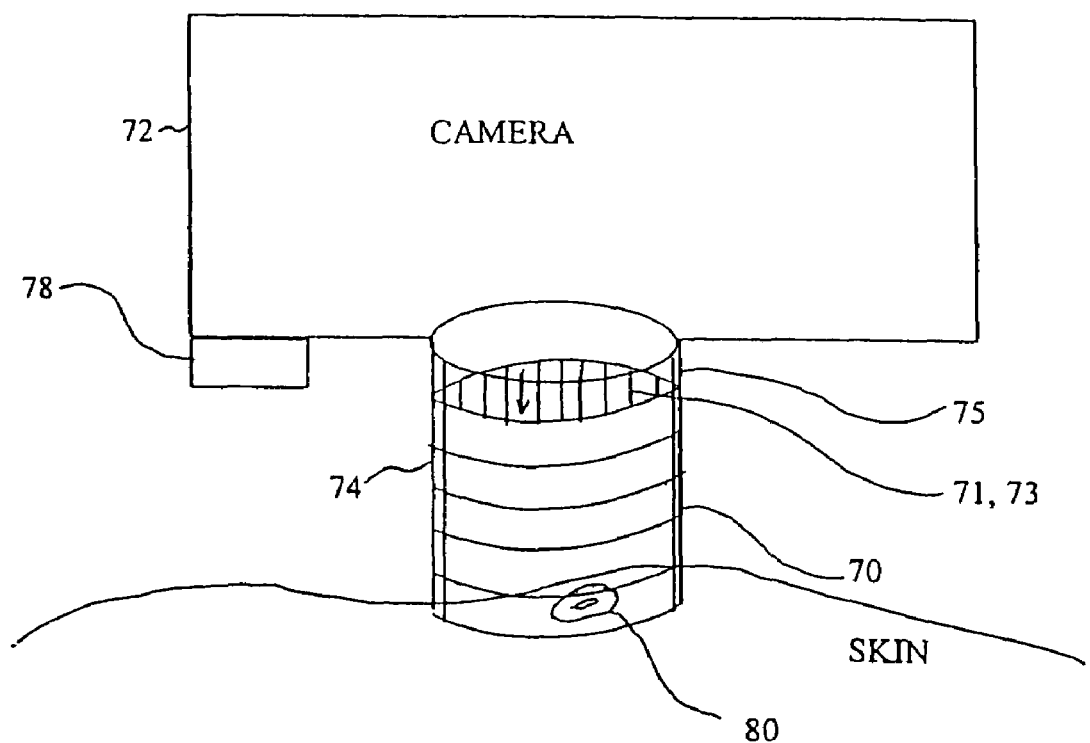
FIG. 6 shows a cylindrical lens stand or lens attachment for performing ELM.

FIG. 6 shows one embodiment of an ELM lens attachment or lens stand for viewing a skin lesion 80. A clear plastic cylinder 70 is used to provide a fixed distance between the skin and a camera lens. Attached to the plastic cylinder is a magnifying lens (or lens with, other properties most appropriate for adapting a particular camera lens for macrophotography) 71 appropriate for the particular camera lens being used. A camera 72 is placed so that its lens rests on the combined lens stand consisting of the plastic cylinder 70 with attached lens of appropriate optical focal length etc 71. If there is apparatus for attaching the lens stand to the camera lens 75 or camera then it is a lens attachment, rather than a lens stand. This apparatus may be a threaded ring attached to lens 71 that fits the camera lens on the camera 72.

The optical properties of the lens stand or lens attachment are specifically designed for ELM photography by either making the plastic cylinder 70 and lens 71 of appropriate polarizing material. Alternatively, in one embodiment a circular piece of polarizing film 73 and a rectangular piece of polarizing film 74 are attached to 71 and 70 as follows. The circular piece of polarizing film 73 is attached to the magnifying lens 71. The rectangular piece of polarizing film 74 is bent so that its short ends meet, forming a cylinder. This cylinder of polarizing film is then inserted into (or around) the plastic cylinder completely covering its internal (or external) surface.

The polarizing axes of the two polarizers are then adjusted with respect to the each other, and with respect to the camera flash (or other light source), to provide crossed-polarization. In other words, the light hitting the skin comes from a light source, for example camera flash, and is first polarized to have a predominant polarization axis. Light reflected from the skin, particularly from layers below the skin surface which become visible with ELM, return through the polarizing film 73, which is oriented orthogonal to the resulting polarization axis of the incident light, before the reflected light passes through the camera lens to the camera sensor. This results in crossed-polarization digital ELM photography. Camera 72 preferably is a digital camera having a flash 78.

What is claimed is:

1. An ELM lens attachment for a camera comprising:
a lens having a first polarization axis; and
a clear cylinder connected to the lens for spacing the camera from a section of skin, the cylinder having a second polarization axis at an angle to the first polarization axis.

2. The ELM lens attachment as recited in claim 1 wherein the cylinder includes a curved polarizing film on an interior surface, the first and second polarization axes being at right angles.

3. The ELM lens attachment as recited in claim 1 wherein the camera is a digital camera.

4. The ELM lens attachment as recited in claim 1 wherein the cylinder is made of polarizing material to provide the second polarization axis.

5. The ELM lens attachment as recited in claim 1 wherein the cylinder includes a polarizing film to provide the second polarization axis.

6. A method for providing ELM photography comprising attaching an ELM lens attachment to a camera, the ELM lens attachment including a cross-polarized cylinder and lens combination.

7. The method as recited in claim 6 wherein the cross-polarized cylinder and lens combination includes a lens having a first polarization axis; and a clear cylinder connected to the lens for spacing the camera from a section of skin, the cylinder having a second polarization axis at an angle to the first polarization axis.

8. The method as recited in claim 6 wherein the cylinder is made of polarizing material to provide the second polarization axis.

9. The method as recited in claim 6 wherein the cylinder includes a polarizing film to provide the second polarization axis.

10. An ELM lens attachment for a camera comprising:
a lens having a first polarization axis; and
a cylinder connected to the lens for spacing the camera from a section of skin, the cylinder having a second polarization axis at an angle to the first polarization axis, the cylinder having a curved section being made of a polarizing material or including a curved polarizing film, the first and second polarization axes being at right angles.

* * * * *